(12) United States Patent
Sievers et al.

(10) Patent No.: US 11,083,574 B2
(45) Date of Patent: Aug. 10, 2021

(54) PROSTHETIC HEART VALVE

(71) Applicant: Hans-Hinrich Sievers, Kronshagen (DE)

(72) Inventors: Hans-Hinrich Sievers, Kronshagen (DE); Michael Scharfschwerdt, Lübeck (DE); Andreas Hof, Lübeck (DE)

(73) Assignee: Hans-Hinrich Sievers, Kronshagen (DE)

( * ) Notice: Subject to any disclaimer, the term of this patent is extended or adjusted under 35 U.S.C. 154(b) by 0 days.

(21) Appl. No.: 15/562,121

(22) PCT Filed: Mar. 23, 2016

(86) PCT No.: PCT/DE2016/200151
§ 371 (c)(1),
(2) Date: Sep. 27, 2017

(87) PCT Pub. No.: WO2016/155730
PCT Pub. Date: Oct. 6, 2016

(65) Prior Publication Data
US 2018/0078366 A1 Mar. 22, 2018

(30) Foreign Application Priority Data
Apr. 2, 2015 (DE) ................ 10 2015 206 099.3

(51) Int. Cl.
*A61F 2/24* (2006.01)

(52) U.S. Cl.
CPC .......... *A61F 2/2418* (2013.01); *A61F 2/2409* (2013.01); *A61F 2210/0057* (2013.01); *A61F 2250/001* (2013.01); *A61F 2250/0004* (2013.01); *A61F 2250/006* (2013.01); *A61F 2250/0071* (2013.01)

(58) Field of Classification Search
CPC ..... A61F 2/2409; A61F 2/2412; A61F 2/2418
See application file for complete search history.

(56) References Cited

U.S. PATENT DOCUMENTS

| 4,106,129 A | * | 8/1978 | Carpentier | A61F 2/2418 623/2.18 |
| 5,163,953 A | | 11/1992 | Vince | |
| 2003/0171805 A1 | * | 9/2003 | Berg | A61F 2/2412 623/2.14 |
| 2006/0195184 A1 | * | 8/2006 | Lane | A61F 2/2409 623/2.38 |
| 2009/0264989 A1 | | 10/2009 | Bonhoeffer et al. | |

(Continued)

FOREIGN PATENT DOCUMENTS

DE 10 2010 051 632 A1 5/2012
DE 10 2010 051 632 B4 9/2013

*Primary Examiner* — Leslie Lopez
(74) *Attorney, Agent, or Firm* — McGlew and Tuttle, P.C.

(57) ABSTRACT

A prosthetic heart valve includes a valve frame (2), on which a plurality of valve leaflets (8) are fixed, and a fastening area for fastening in a blood vessel, which axially adjoins the valve frame (2). A stabilizing ring (14) is arranged in the fastening area. The stabilizing ring (14) defines a predetermined shape and a predetermined diameter of the fastening area and has at least one predetermined expansion point (22), whereby it is possible to expand the stabilizing ring (14) by an action of radial force on an inner circumference.

18 Claims, 7 Drawing Sheets

(56) References Cited

U.S. PATENT DOCUMENTS

| | | |
|---|---|---|
| 2010/0076549 A1 | 3/2010 | Keidar et al. |
| 2013/0274872 A1 | 10/2013 | Vesely |
| 2014/0188219 A1 | 7/2014 | Conklin et al. |
| 2014/0188221 A1 | 7/2014 | Chung et al. |

* cited by examiner

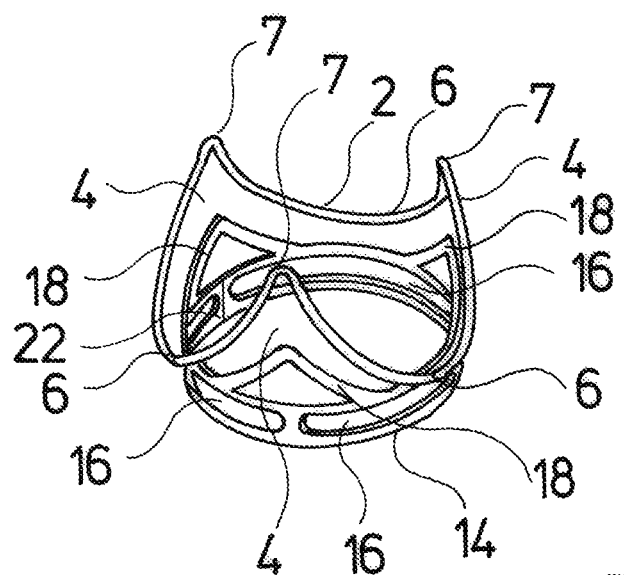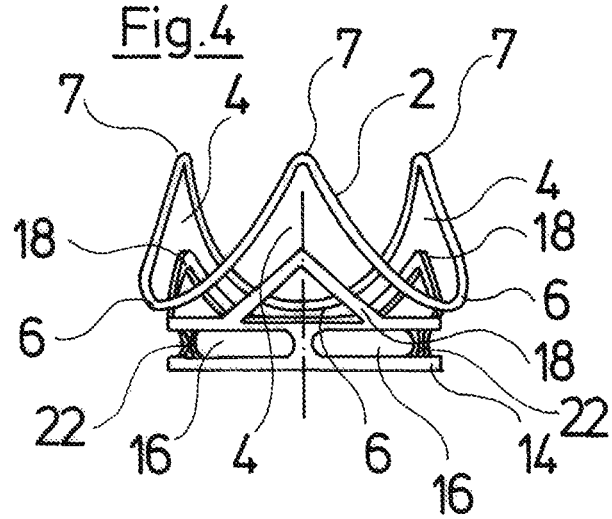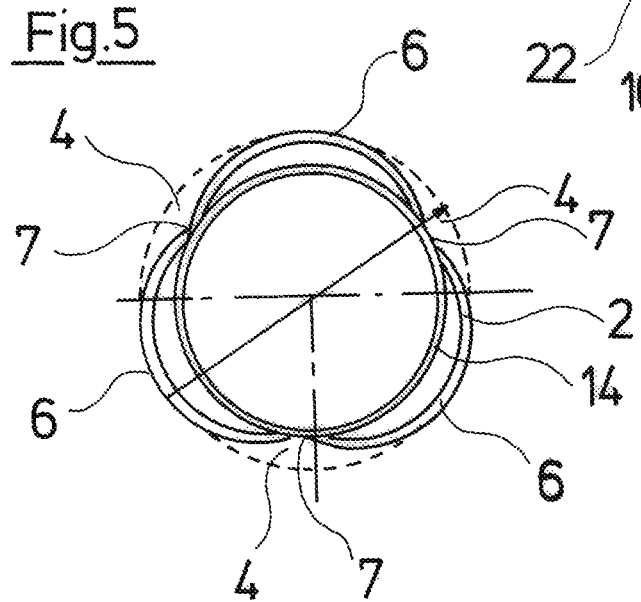

PROSTHETIC HEART VALVE

CROSS REFERENCE TO RELATED APPLICATIONS

This application is a United States National Phase Application of International Application PCT/DE2016/200151, filed Mar. 23, 2016, and claims the benefit of priority under 35 U.S.C. § 119 of German Application 10 2015 206 099.3, filed Apr. 2, 2015, the entire contents of which are incorporated herein by reference.

FIELD OF THE INVENTION

The invention relates to heart valve prosthesis, in particular to heart valve prosthesis for the replacement of the aortic valve.

BACKGROUND OF THE INVENTION

A biological heart valve prosthesis for the replacement of the aortic valve is known for example from DE 10 2010 051 632. Concerning such biological heart valve prostheses, the problem of them wearing and possibly having to be replaced exists.

SUMMARY OF THE INVENTION

With regard to this problem, it is an object of the invention to improve a heart valve prosthesis to the extent that it can be replaced by a further heart valve prosthesis in a simple manner.

The heart valve prosthesis according to the invention comprises a valve frame, to which several valve leaflets are fastened. The valve leaflets are preferably of a biological material, which is to say it is the case of a biological heart valve prosthesis. Particularly preferably, three valve leaflets are provided and the valve frame is accordingly shaped with three arched holding elements which run out into three commissures and which carry the valve leaflets. The valve frame is preferably configured of metal and is elastically deformable to a certain extent.

A fastening region for fastening in a blood vessel connects to the valve frame in an axial manner, which is to say in the flow direction or counter to this. In particular, a sewing ring (suture ring), on which the heart valve prosthesis is sewn to a surrounding blood vessel can be situated in this fastening region. A stabilization ring which defines a predefined shape and a predefined diameter of the fastening region is arranged in the fastening region. In particular, this stabilization ring preferably defines the maximal flow cross section of the heart valve prosthesis. The stabilization ring serves for possibly expanding the blood vessel, so that the maximal flow cross section is indeed achieved.

According to the invention, the stabilization ring comprises at least one predetermined stretching location which permits the expansion of the stabilization ring by way of a radial force action which acts upon its inner periphery from the inside. The predetermined stretching location is configured such that it extends preferably over the whole axial length of the stabilization ring, so that this ring can expand in the peripheral direction given a force action.

This characteristic of the stabilization ring can be utilized in order to replace the heart valve prosthesis with new heart valve prosthesis in the case of wear, by way of this new prosthesis being inserted into the inside of the heart valve prosthesis according to the invention. For example, this can be a transcatheter heart valve prosthesis which via a catheter is brought into the vessel and into the inside of an existing heart valve prosthesis. The new heart valve prosthesis is then expanded there, wherein the described force acts upon the inner periphery of the stabilization ring of the heart valve prosthesis according to the invention, so that the stabilization ring is stretched at its predetermined stretching location and expands (widens). The heart valve prosthesis can therefore be pressed apart in the radial direction, so that space for a new heart valve prosthesis is created in the inner space and this new heart valve prosthesis is then fixed in the inside of the existing heart valve prosthesis, in particular non-positively and/or positively. Here, the valve leaflets of the old heart valve prosthesis are likewise pressed outwards onto the vessel wall. The expansion of the stabilization ring permits a new heart valve prosthesis to be inserted without the inner cross section being significantly reduced in size. In contrast, the stabilization ring as well as the surrounding tissue of the blood vessel can then be stretched by the new heart valve prosthesis so that an adequate flow cross section is achieved again.

The predetermined stretching (expanding) location is preferably configured in a manner such that a predefined limit force must be exceeded when applying force for expanding the stabilization ring. This limit force is preferably selected such that this limit force is not exceeded on normal application and in particular on implanting the heart valve prosthesis, so that the stabilization ring can be inserted into the blood vessel without damage to it, which is to say in a non-stretched manner and can be fixed there in the manner described above. The limit force is preferably selected such that it is not reached until insertion of a new heart valve prosthesis with the help of a catheter. Here, such a large force is then applied from the inside that the limit force is exceeded and the predetermined stretching location stretches so that the stabilization ring is expanded (widened) in the peripheral direction.

According to a further preferred embodiment, the stabilization ring is manufactured from metal, in particular from nitinol, titanium or another suitable alloy. The stabilization ring can alternatively also be manufactured of a suitable plastic.

The stabilization ring preferably has such a strength that it withstands a force which acts upon it radially from the outside and which is exerted by the surrounding blood vessel when it stretches, without a plastic deformation of the stabilization ring occurring. The stabilization ring preferably withstands a greater radial pressing force from the outside than from the inside.

According to a particularly preferred embodiment, the at least one predetermined stretching location can be configured as a predetermined breakage location, at which the stabilization ring tears in a defined manner given a force action upon its inner periphery. This means that the stabilization ring is separated at the predetermined stretching location in a defined manner given an adequate force action, so that this ring can expand.

Instead of a predetermined breakage location, the predetermined stretching location can also be configured as a separation location, at which parts of the stabilization ring which lie opposite one another in the peripheral direction bear on one another such that the stabilization ring can withstand a pressing force from the outside, but in the case of a force action from the inside expands in the peripheral direction as a result of the separation location widening.

According to a further preferred embodiment, the predetermined stretching location is configured in a manner such that it is plastically stretched in the peripheral direction of the stabilization ring given a force action. The expansion of the stabilization ring at the predetermined stretching location is therefore irreversible. This means that the heart valve prosthesis retains its expanded shape after the discontinuation of the force action. Such a predetermined stretching location is preferably configured such that it does not completely tear, so that the stabilization ring is retained as a closed ring.

According to the invention, at least one predetermined stretching location or predetermined breakage location is provided in the stabilization ring. However, according to a particularly preferred embodiment, several predetermined stretching locations or predetermined breakage locations can be provided, wherein these are preferably uniformly distributed over the periphery. Particularly preferably, three predetermined stretching location are provided, wherein the predetermined stretching locations are preferably situated essentially at the angular positions of the commissures of the heart valve prosthesis. A uniform expansion amid the application of force can be achieved in this manner, wherein the valve frame can also preferably deform in the region of the commissures such that it participates in the expansion.

Moreover, it is to be understood that combinations of predetermined stretching locations which permit a plastic deformation, predetermined breakage locations and/or separation locations can also be used in the stabilization ring, in order to permit the desired characteristics of the stabilization ring, specifically a resistance capability with respect to pressing forces from the outside and an expansibility given a force action from the inside.

According to a further preferred embodiment, the stabilization ring is arranged inside a sheathing. Such a sheathing can be configured for example of a fabric material which also envelopes the valve frame. Such a material can create the connection to a sewing ring or simultaneously serve as a sewing ring, through which a thread is led for sewing.

The sheathing is preferably configured such given the expansion of the stabilization ring, it stretches accordingly, which is to say to the same extent as the stabilization ring. The sheathing does not therefore inhibit the expansion of the stabilization ring.

Alternatively, the sheathing can be configured in a manner such it tears, preferably at least one predetermined breakage location on expansion of the stabilization ring. It is thus also ensured that the sheathing does not compromise the expansion of the stabilization ring. In order to render the tearing possible, the material of the sheathing is selected such that on exceeding a limit force by way of tensile forces acting in the peripheral direction, it tears at at least one predetermined breakage location is a defined manner or at an arbitrary location if the complete material is selected such that it tears at a limit force. The arrangement of a predetermined breakage location or several predetermined breakage locations has the advantage of a defined tearing, by which means it is ensured that no loose parts of the sheathing remain.

According to a further preferred embodiment, the stabilization ring is connected to the valve frame in a force-decoupled manner. This permits the valve frame to be able to move with respect to the stabilization ring and in particular to be able to expand with respect to the stabilization ring. The arches of the valve frame can therefore extend into the Sinus aortae, as is known from DE 10 2010 051 632. A maximal flow cross section is achieved in this manner. Moreover, on inserting a new heart valve prosthesis, the valve frame can therefore expand independently of the stabilization ring, in order to create space for the new heart valve prosthesis. On inserting a new heart valve prosthesis, the stabilization ring expands on account of the described predetermined breakage locations or predetermined stretching locations, whilst the force-decoupled valve frame expands in the radial direction solely due to its elasticity and/or plastic deformability, preferably independently of the predetermined breakage locations and/or predetermined stretching locations in the stabilization ring.

The valve frame is particularly preferably configured in an elastically deformable manner. This on the one hand assists the opening and closure movement of the valve leaflets and on the other hand permits the valve frame to be able to be reduced in its diameter or cross section for insertion and to be able to subsequently expand again, in particular into the Sinus aortae as described previously. Moreover, as described above, the valve frame can also still expand by a further amount on expansion of the stabilization ring, in order in the inside to create space for a new heart valve prosthesis.

The invention is hereinafter described by way of example and by way of the accompanying figures. The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a perspective view of the valve frame and of the stabilization ring of the heart valve prosthesis according to FIGS. 1 and 2;

FIG. 4 is a lateral view of the valve frame and of the stabilization ring according to FIG. 3;

FIG. 5 is a plan view of the arrangement of the valve frame and of the stabilization ring according to FIG. 4, from above;

DESCRIPTION OF THE PREFERRED EMBODIMENTS

Figure 1:
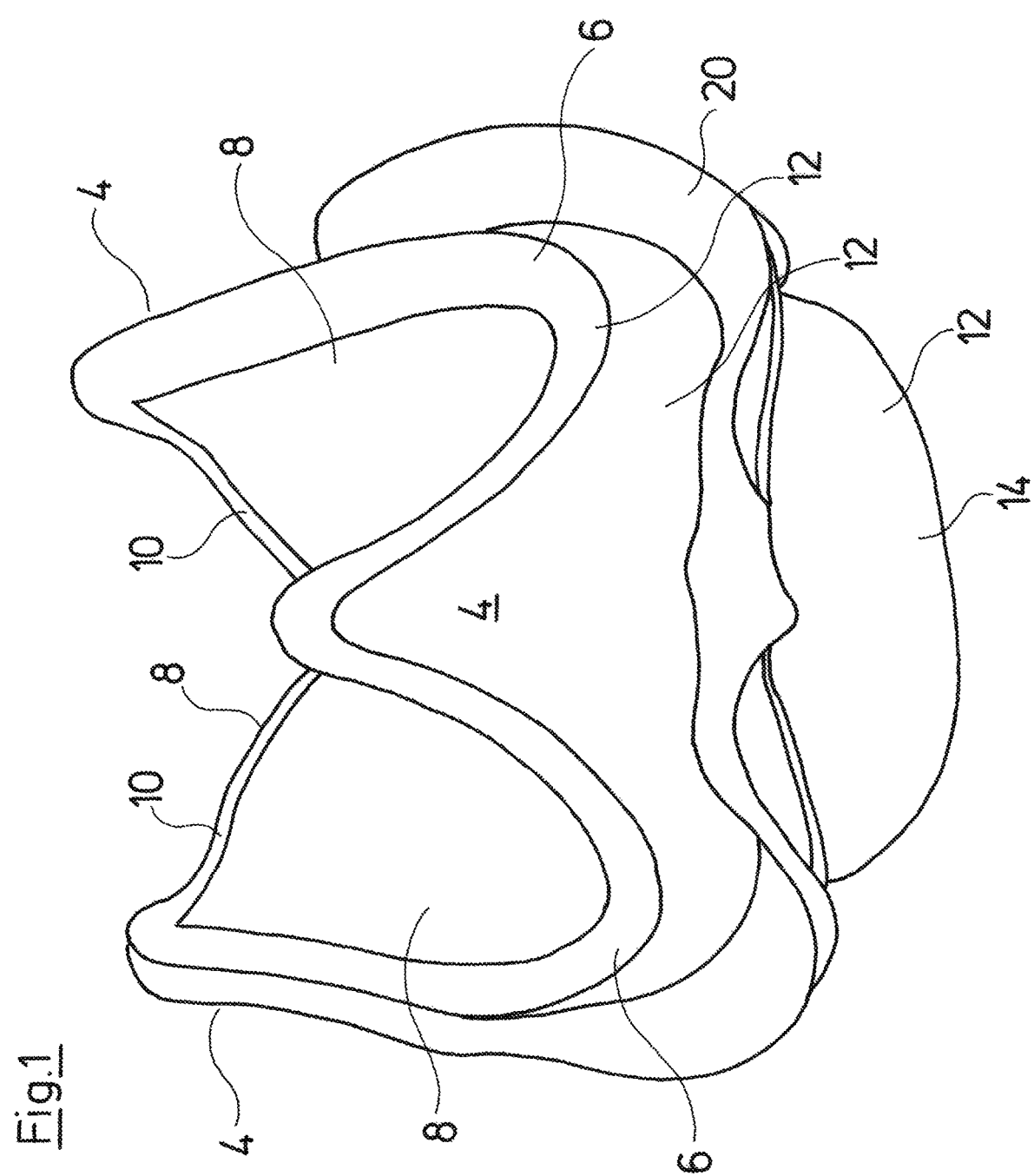
FIG. 1 is a perspective view of a heart valve prosthesis according to the invention.
Figure 2:
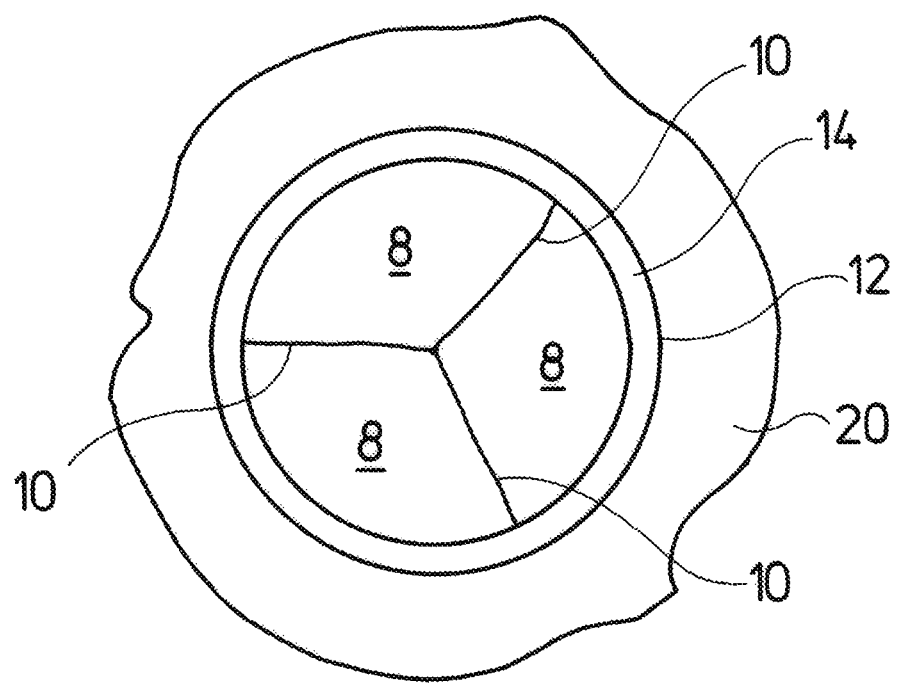
FIG. 2 is a plan view of the heart valve prosthesis according to FIG. 1, from below.

Referring to the drawings, the heart valve prosthesis according to the invention, which is shown in FIGS. 1 and 2, in its inside, as is shown in FIGS. 3 to 5, comprises a valve frame 2 having three arches 6 which at their ends are connected to one another by way of connecting arches 7 and thus form three commissures 4. The valve frame 2 is formed from a metallic wire which is elastically deformable. The three arches 6 carry three valve leaflets 8 of biological material. These semilunar valves or valve leaflets 8 abut on another at three contact edges 10 and are sealed to one another there. For opening, the valve leaflets 8 move radially outwards, so that they disengage at the contact edges 10 and release a central opening.

The valve frame 2 is otherwise enveloped by a sheathing 12 of a textile or fabric material which also extends over the commissures 4 and peripherally closes these. A first downstream axial end of the heart valve prosthesis is defined by the tips or connecting arches 7 of the commissures 4. A fastening region is formed at the opposite, upstream axial end. There, a stabilization ring 14 is located in the inside of the sheathing 12. The stabilization ring 14 is manufactured of metal and comprises a defined annulus shape. The inner cross section of the stabilization ring 14 corresponds essentially to the inner cross section between the tips of the commissures 14 and defines the maximal flow cross section through the heart valve prosthesis. This can be recognized particularly well from FIG. 5.

The stabilization ring 14 is configured rigidly compared to the valve frame 2, which is to say it has a lower elasticity or deformability than the valve frame 2. In particular, the stabilization ring 14 is essentially not elastically deformable in the radial direction. The stabilization ring 14 comprises openings 16 in the radial direction. These openings 16 permit sewing material which is to say threads to be led through the stabilization ring 14, in order to fasten the heart valve prosthesis on the stabilization ring 14 in a blood vessel. The stabilization ring 14 at an axial end moreover comprises three commissure supports 18 which extend into the commissures 4 of the valve frame 2. These commissure supports 18 support the sheathing 12 in the region of the commissures 4, so that these are held in a defined shape.

Figure 6:
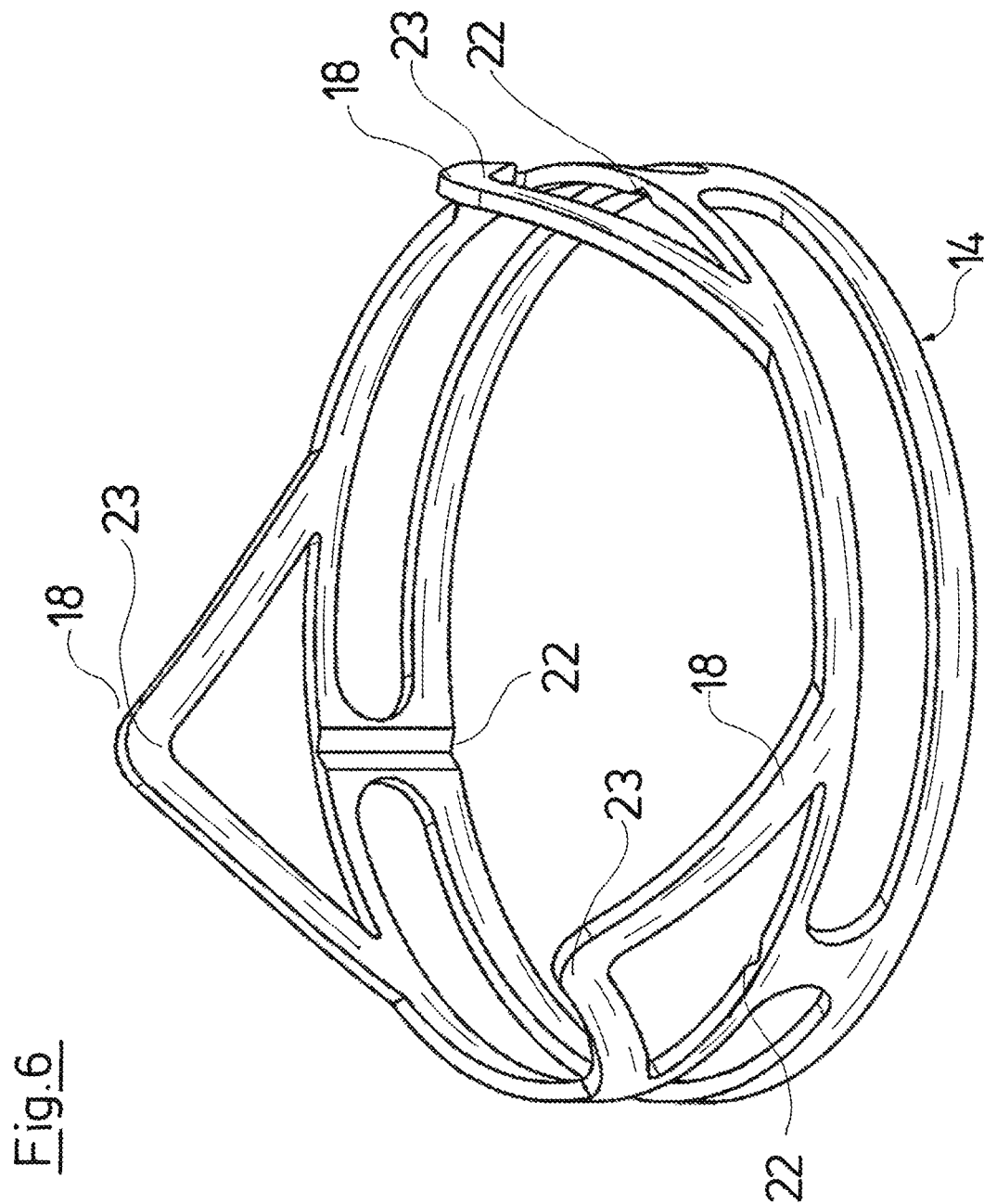
FIG. 6 is a perspective detailed view of a stabilization ring according to the invention.

As is to be particularly recognized in FIG. 6, the stabilization ring 14 moreover comprises axially extending notches 22 on the inner side at the angular positions of the commissure supports 18. The notches 22 extend parallel to the flow direction through the heart valve prosthesis and form predetermined breakage locations. If an adequately large force is exerted from the inner periphery onto the stabilization ring 14, then the stabilization ring tears or breaks in the region of the notches 22, which is to say that the predetermined breakage locations which are formed there break and the stabilization ring 14 can expand in the peripheral direction, so that its obtains a larger diameter. Here, a deformation of the commissure supports 18 occurs, and for this, these at their tips are configured in a deformable manner with predetermined deformation locations or predetermined stretching locations 23. Alternatively, these can also be configured in the manner shown in FIG. 9. Predetermined breakage locations could alternatively also be provided in the region of the commissure supports 18 at their tips. The sheathing 12 is simultaneously configured such that it can expand with the stabilization ring 14 when this ring is broken at its notches 22. This configuration permits the insertion of a further heart valve prosthesis into the inside of this heart valve prosthesis, and permits this further heart valve prosthesis to then unfold radially and press into the inner region of the stabilization ring 14 amid the application of force, so that this ring breaks at its notches 22 and expands and together with the fastening region of the new heart valve prosthesis is pressed against the surrounding tissue of the blood vessel, so that this is likewise expanded. The new heart valve prosthesis can therefore be fixed in the blood vessel amid the expansion of the old heart valve prosthesis, wherein the flow cross section is not significantly reduced in size. This permits a new heart valve prosthesis to be inserted by way of a catheter, without having to remove the previous heart valve prosthesis.

It is to be understood that a predetermined stretching location can also be formed instead of a predetermined breakage location 22, according to which predetermined stretching location the material only plastically deforms under the application of force, so that the stabilization ring 14 expands in the peripheral (circumferential) direction and widens its diameter by way of this. Moreover, only a notch 22 could also be provided. The material could also be configured in a thinned-out or weakened fashion in a manner other than by way of a notch 22, in order to create the predetermined breakage location or predetermined stretching location.

Figure 7:
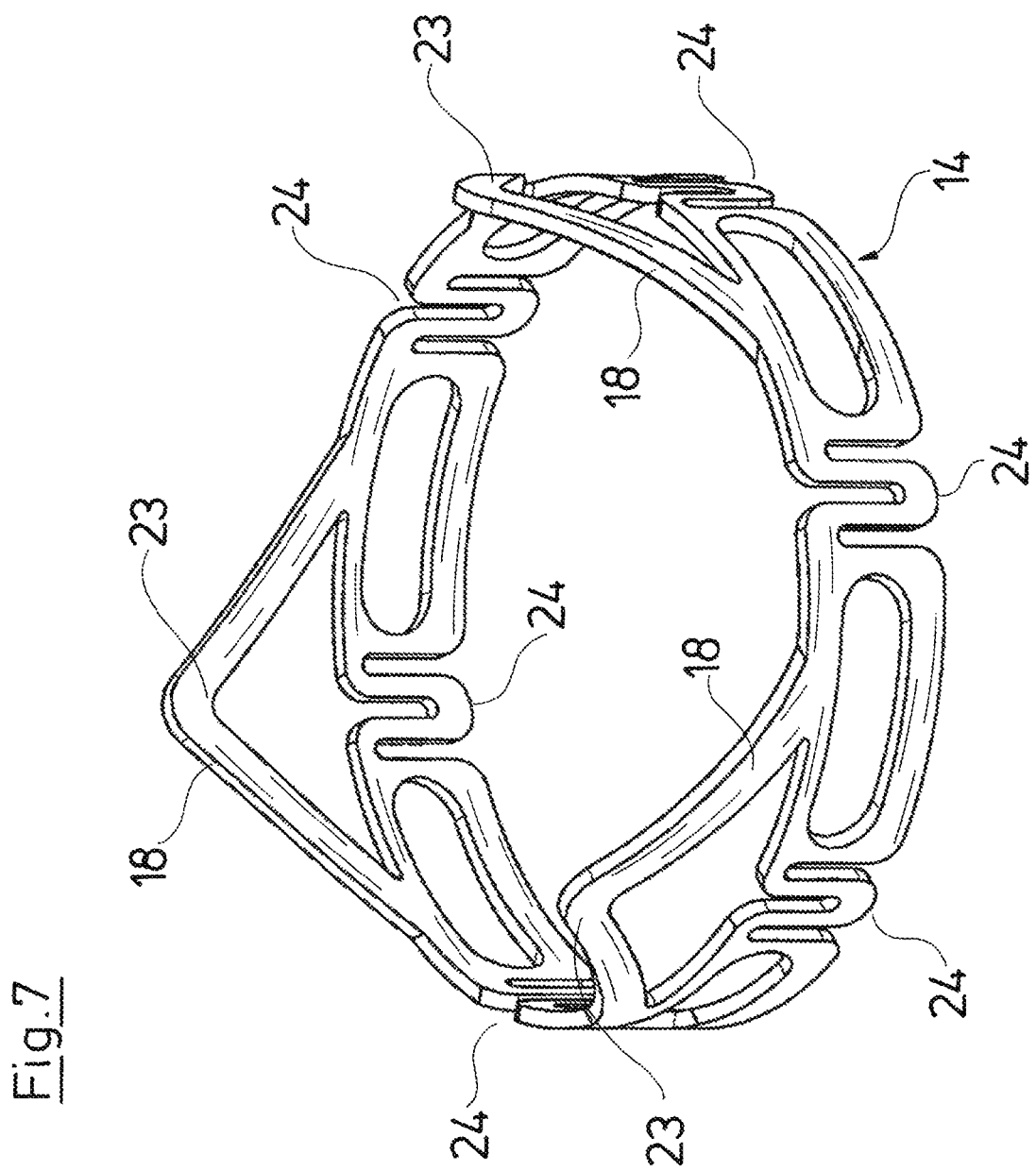
FIG. 7 is a second embodiment of a stabilization ring according to the invention.

FIG. 7 shows an alternative stabilization ring 14 which instead of the notches 22 functioning as predetermined breakage locations comprises six predetermined stretching locations 24. The predetermined stretching locations 24 are formed by way of bendings and windings of the material transverse to the peripheral direction of the stabilization ring 14, so that in the regions of the predetermined stretching locations 24 the material of the stabilization ring can be plastically deformed such that the stabilization ring 14 stretches in the peripheral direction. This is effected by way of bending open the windings at the predetermined stretching locations 24. The commissure supports 18 comprise predetermined stretching locations 23 as have been described by way of FIG. 6.

Figure 8:
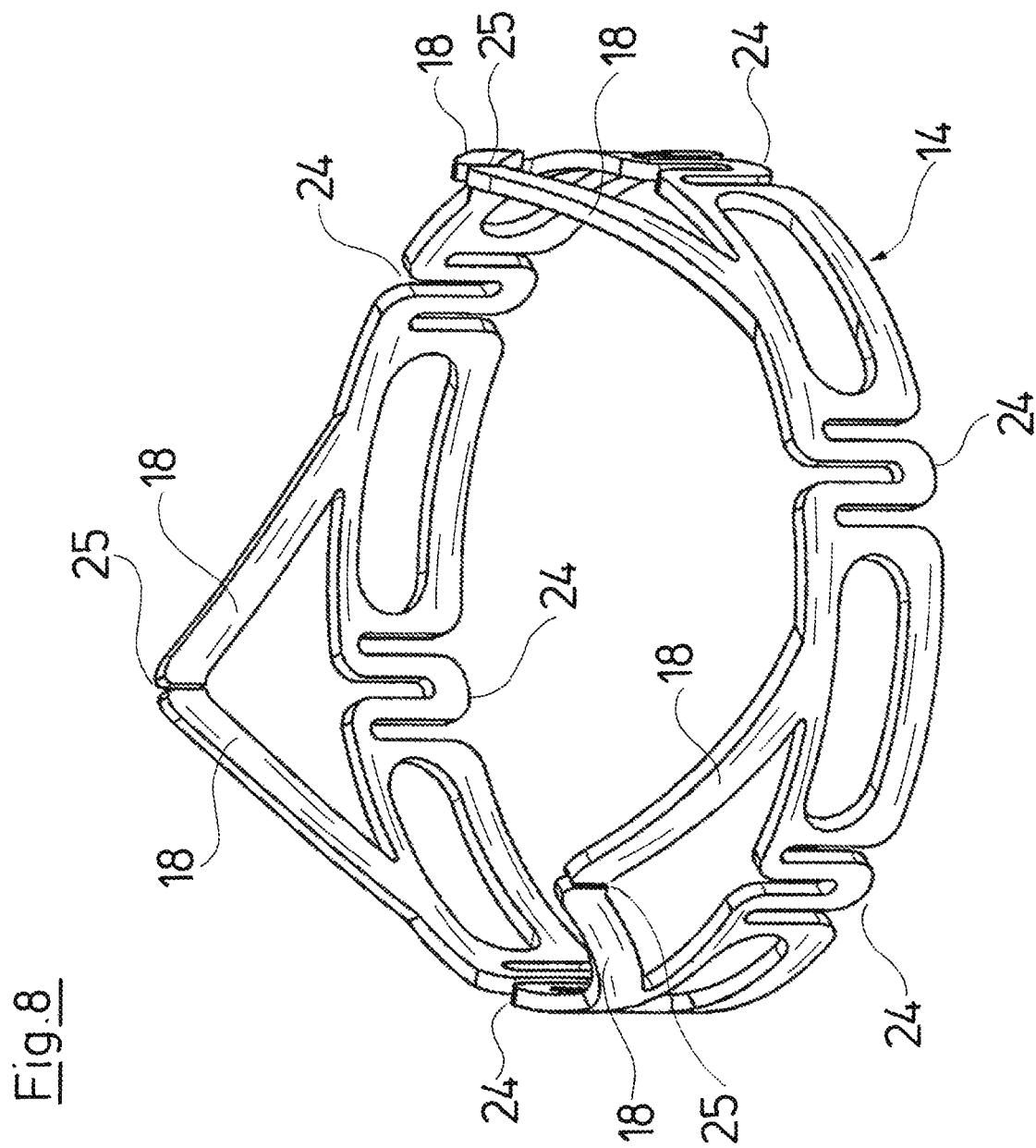
FIG. 8 is a third embodiment of a stabilization ring according to the invention.

Predetermined stretching locations 24 as have been described by way of FIG. 7 are also formed with regard to the stabilization ring 14 according to FIG. 8. In contrast to the embodiment example according to FIG. 7, it is not predetermined stretching locations 23 but separation locations 25 which are formed at the tips of the commissure supports 18. At the separation locations 23, the webs which form the commissure supports 18 comprise a continuous gap or continuous joint, which is configured such that the opposite sides of the gap come to bear on one another in order to transmit a compression force. A tensile force however cannot be transmitted, and this leads to an expansion of the gap at the separation locations 25 so that when the predetermined stretching locations 24 expand in the peripheral direction, the commissure supports 18 can also expand in the peripheral direction by way of enlarging the separation locations 25.

Figure 9:
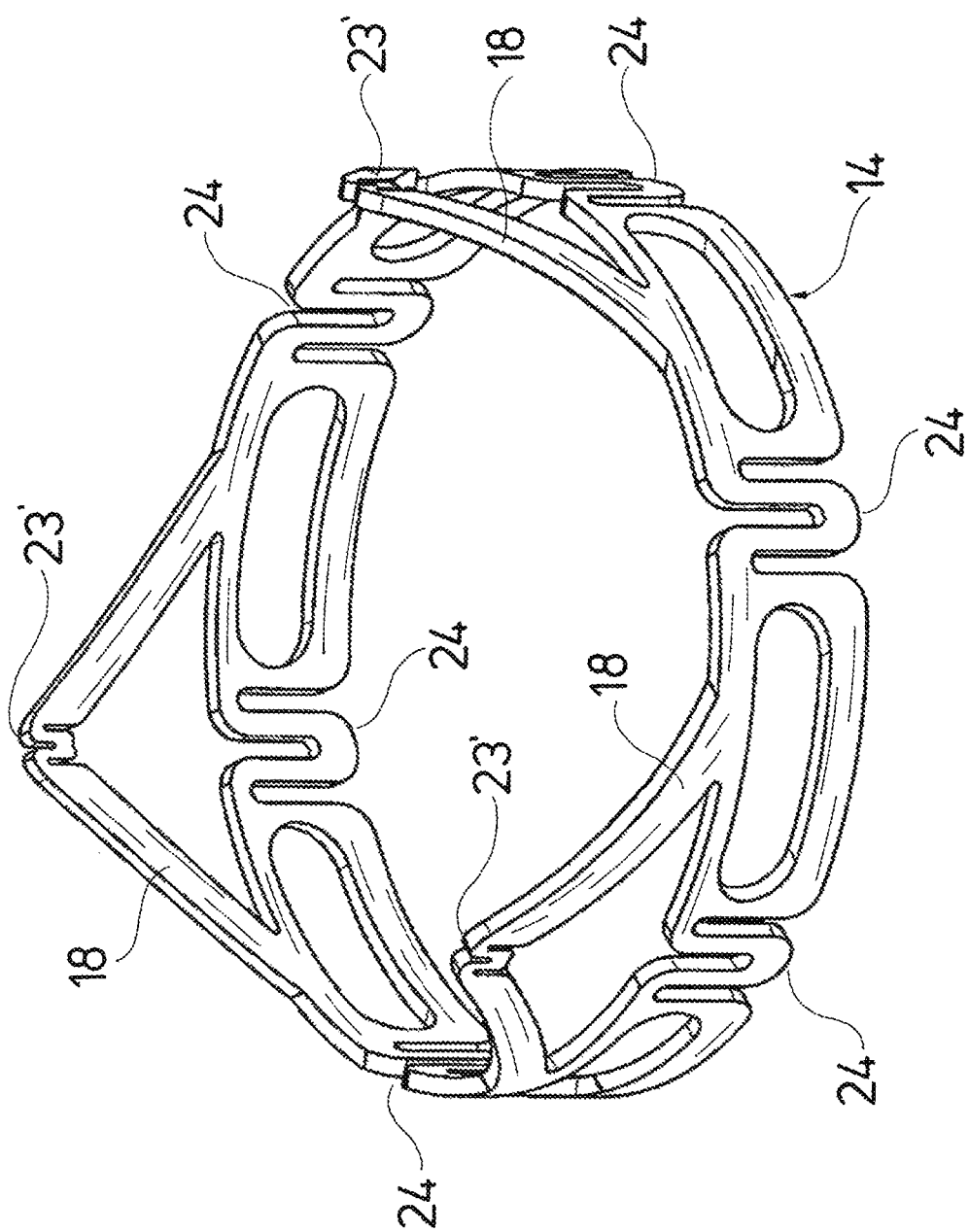
FIG. 9 is a fourth embodiment of a stabilization ring according to the invention.

A further variant of a stabilization ring 14 is shown in FIG. 9. This variant corresponds essentially to the variant according to FIG. 7, wherein here too the predetermined stretching locations 23' in the commissure supports 18 are formed by windings or arches in the webs forming the commissure supports 18. These predetermined stretching locations 34 can also stretch in the peripheral direction by way of widening out the arches.

The notches 22 as well as the predetermined stretching locations 23, 23' and 24 are preferably configured such that they do not tear until exceeding a predefined limit force. This limit force is selected such that such a limit force does not act upon the stabilization ring 14 on inserting the heart valve prosthesis into a blood vessel and during its normal application, so that this ring is shape-stable in the described manner. It is only on inserting a new heart valve prosthesis by way of a catheter which is brought into the inside of the described heart valve prosthesis that a sufficiently large force can be mustered so that the limit force is exceeded and the notches 22 tear, or the predetermined stretching locations 23, 23' and 24 stretch in the peripheral direction.

It is to be understood that the described predetermined stretching locations 23, 23' as well as the separation locations 25 can also be applied together with predetermined breakage locations or differently configured predetermined stretching locations. Moreover, it is to be understood that separation locations which permit an expansion in the peripheral direction but which permit the stabilization ring 14 to accommodate compressive forces which act radially upon the stabilization ring 14 from the outside can also be provided in the stabilization ring 14 instead of the notches 22 or predetermined stretching locations 24. Moreover, it is to be understood that other numbers of predetermined breakage locations 22 or predetermined stretching locations 23, 23', 24 as well as separation locations 25 can also be applied, in order on the one hand to permit a sufficient stability of the stabilization ring with respect to external compressive forces and on the other hand to permit an expansion given the application of a force from the inside.

The valve frame 2 and the stabilization ring 14 are not directly connected to one another, as can be recognized in FIGS. 3 and 4, which represent the arrangement of the valve frame 2 and of the stabilization ring 14 in the inside of the heart valve prosthesis shown in FIG. 1. In contrast, the valve frame 2 and the stabilization ring 14 are connected to one another solely by way of a flexible sheathing 12 of textile or fabric material, so that a force-decoupled connection between the valve frame 2 and the stabilization ring 14 is given. The valve frame 2 can move relative to the stabilization ring 14 on account of the flexibility of the fabric material of the sheathing 12. This permits an elastic deformability of the valve frame 2 in particular in the radial direction, whereas the stabilization ring 14 is not deformed on insertion into a blood vessel due to its rigid configuration. Despite this, the stabilization ring 14 and the valve frame 2 with the valve leaflets 8 formed therein, by means of the sheathing 12 form a premanufactured construction unit which in its entirely can be inserted into a blood vessel, without assembly activities or a sewing between the stabilization ring 14 and the valve frame 2 with the valve leaflet 8 yet becoming necessary on operation.

FIGS. 3 to 5 show the non-deformed, relaxed condition of the valve frame 2. It can be recognized that in this condition, the arches 6 of the valve frame 2 extend radially beyond the outer periphery of the stabilization ring 14, whereas the commissures 4 are situated essentially on the periphery of the stabilization ring 14. The arches 6 of the valve frame 2 can therefore extend into the Sinus aortae in the implanted condition and thus release a maximal inner cross section which corresponds essentially to the natural cross section of the aorta. For this, the shown heart valve prosthesis with regard to its dimensioning is matched to the respective blood vessel, so that the inner diameter of the stabilization ring 14 corresponds essentially to the natural inner diameter of the aorta or is slightly larger. A certain expansion or widening of the tissue of the blood vessel can thus be achieved on insertion, so that as a whole the flow cross section through this heart valve prosthesis is not restricted. For this, the stabilization ring 14 is preferably configured such that it can accommodate radial compressive forces from the outside, without a breakage or tearing of the predetermined breakage locations formed by the notches 22 occurring. These predetermined breakage locations are therefore configured such that they can accommodate larger compressive forces than tensile forces.

As is known from DE 10 2010 051 632 B4, the valve frame 2 can be moved radially inwards for insertion, so that the arches 6 are deformed radially inwards and the maximum outer diameter is defined by the stabilization ring 14. The sewing is therefore simplified. This deformation of the valve frame 2 can be released after the sewing, so that the arches 6 then expand again on account of their elasticity, as described beforehand, and in particular can expand into the Sinus aortae. This is particularly possible on account of the flexible, force-decoupled connection of the valve frame 2 to the stabilization ring 14. The stabilization ring 14 is configured in an adequately rigid manner, in order to define the inner cross section of the heart valve prosthesis and for this to be firmly inserted into the blood vessel, which is to say into the aorta and to be fixed there. Here, the stabilization ring 14 specifies a defined size and shape of the heart valve prosthesis and in particular of its flow cross section.

The stabilization ring 14 can be manufactured of a shape memory alloy, such as nitinol, so that it is possible to radially deform it before the insertion, so that its outer cross section is reduced. After the insertion, it can then move back into the shown initial shape by way of a change in temperature and then be firmly fixed in a blood vessel, where, as a rigid structure, it then defines the desired cross section.

A sewing ring 20 of textile or fabric material which overlaps the stabilization ring 14 at the outer periphery is moreover arranged on the sheathing 12 at the outer periphery. This permits the heart valve prosthesis to be sewn into the blood vessel such that the tissue of the blood vessel comes to lie between the stabilization ring 14 and the sewing ring 20, and the threads for sewing can be led through the sewing ring 20, the body tissue lying therebetween and then through the stabilization ring 14. Here, the sewing material is led through the sheathing surrounding the stabilization ring 14 and through the openings 16 in the stabilization ring 14. The stabilization ring 14 thus forms a counter surface on sewing, so that additional felts as counter surfaces are not necessary.

While specific embodiments of the invention have been shown and described in detail to illustrate the application of the principles of the invention, it will be understood that the invention may be embodied otherwise without departing from such principles.

The invention claimed is:

1. A heart valve prosthesis comprising:
a valve frame on which valve leaflets are directly fastened; and
a fastening region which connects axially onto the valve frame, for fastening in a blood vessel, wherein a stabilization ring is arranged in the fastening region, said stabilization ring defining a predefined shape and a predefined diameter of the fastening region, the stabilization ring being connected to the valve frame in such a force-decoupled manner that the valve frame is movable with respect to the stabilization ring and the valve frame is movable to expand with respect to the stabilization ring independent of expansion of the stabilization ring, and the stabilization ring comprising at least one predetermined stretching location which permits the stabilization ring to expand by way of a radial application of force upon a stabilizing ring inner periphery, the stabilization ring comprising a strength that withstands a force which acts radially upon the stabilization ring from a position outside of the stabilization ring via a blood vessel without plastic deformation of the stabilization ring such that the stabilization ring maintains the blood vessel in an open state, wherein a greater force is applied from inside the stabilization ring and irreversibly plastically deforms the stabilization ring at the predefined stretching location such that a shape of the stabilization ring does not change after the greater force is applied from inside the stabilization ring, wherein the stabilization ring withstands a greater radial pressing force from outside the stabilization ring than from inside the stabilization ring.

2. The heart valve prosthesis according to claim 1, wherein the predetermined stretching location is configured such that a predefined force must be exceeded for expanding the stabilization ring given the application of force.

3. The heart valve prosthesis according to claim 1, wherein the stabilization ring is manufactured from metal.

4. The heart valve prosthesis according to claim 1, wherein the at least one predetermined stretching location is configured as a predetermined breakage location, at which the stabilization ring tears in a defined manner given the application of force upon the stabilizing ring inner periphery.

5. The heart valve prosthesis according to claim 1, wherein the predetermined stretching location is configured such that the predetermined stretching location is plastically stretched in a peripheral direction of the stabilization ring given the application of force.

6. The heart valve prosthesis according to claim 1, further comprising a sheathing, wherein the stabilization ring is arranged in an inside of the sheathing.

7. The heart valve prosthesis according to claim 6, wherein the sheathing is stretchable in a manner such that given an expansion of the stabilization ring, the sheathing stretches accordingly.

8. The heart valve prosthesis according to claim 6, wherein the sheathing is configured such that the sheathing tears at at least one predetermined breakage location, when the stabilization ring is expanded.

9. The heart valve prosthesis according to claim 6, wherein only the sheathing connects the valve frame to the stabilization ring.

10. The heart valve prosthesis according to claim 1, wherein the stabilization ring is connected to the valve frame via a flexible connection.

11. The heart valve prosthesis according to claim 1, wherein the valve frame is configured to be elastically deformably.

12. The heart valve prosthesis according to claim 1, wherein at least a portion of the valve frame extends radially beyond an outer periphery of the stabilizing ring with respect to a longitudinal axis of the stabilizing ring when the valve frame is in a non-deformed state.

13. The heart valve prosthesis according to claim 1, wherein the valve frame is located at spaced location from the stabilizing ring, the valve frame being expandable in a radial direction to a position beyond the stabilizing ring.

14. A heart valve prosthesis comprising:
a valve frame on which valve leaflets are directly fastened; and
a fastening region which connects axially onto the valve frame, for fastening in a blood vessel, wherein a stabilization ring is arranged in the fastening region, said stabilization ring defining a predefined shape and a predefined diameter of the fastening region, the stabilization ring being located at a spaced location from the valve frame, wherein the stabilization ring is connected to the valve frame such that the valve frame is at least radially movable and expandable independent of at least radial movement and expansion of the stabilization ring with respect to a longitudinal axis of the stabilization ring, the stabilization ring comprising at least one predetermined stretching location which permits the stabilization ring to expand by way of a radial application of force upon a stabilizing ring inner periphery, the stabilization ring comprising a strength that withstands a force which acts radially upon the stabilization ring from a position outside of the stabilization ring via a blood vessel without plastic deformation of the stabilization ring such that the stabilization ring maintains the blood vessel in an open state, wherein a greater force is applied from inside the stabilization ring and irreversibly plastically deforms the stabilization ring at the predefined stretching location such that a shape of the stabilization ring is retained after applying the greater force to stabilization ring, wherein the stabilization ring withstands a greater radial pressing force from outside the stabilization ring than from inside the stabilization ring.

15. The heart valve prosthesis according to claim 14, wherein at least a portion of the valve frame extends radially beyond an outer periphery of the stabilizing ring with respect to a longitudinal axis of the stabilizing ring when the valve frame is in a non-deformed state, wherein each portion of the stabilization ring is located radially inward of the valve frame when the valve frame is in the non-deformed state.

16. The heart valve prosthesis according to claim 14, further comprising a sheathing, wherein at least a portion of the stabilization ring is arranged in an interior space of the sheathing.

17. The heart valve prosthesis according to claim 16, wherein only the sheathing connects the valve frame to the stabilization ring.

18. A heart valve prosthesis comprising:
a plurality of valve leaflets;
a valve frame, said plurality of valve leaflets being in contact with said valve frame; and
a fastening region which connects axially onto the valve frame, for fastening in a blood vessel, wherein a stabilization ring is arranged in the fastening region, said stabilization ring defining a predefined shape and a predefined diameter of the fastening region, the stabilization ring being connected to the valve frame in such a force-decoupled manner that the valve frame is movable with respect to the stabilization ring and the valve frame is movable to expand with respect to the stabilization ring independent of expansion of the stabilization ring, and the stabilization ring comprising at least one predetermined stretching location which permits the stabilization ring to expand by way of a radial application of force upon a stabilizing ring inner periphery, the stabilization ring comprising a strength that withstands a force which acts radially upon the stabilization ring from a position outside of the stabilization ring via a blood vessel without plastic deformation of the stabilization ring such that the stabilization ring maintains the blood vessel in an open state, wherein a greater force is applied from inside the stabilization ring and irreversibly plastically deforms the stabilization ring at the predefined stretching location such that a shape of the stabilization ring does not change after the greater force is applied from inside the stabilization ring, wherein the stabilization ring withstands a greater radial pressing force from outside the stabilization ring than from inside the stabilization ring.

* * * * *